US012767950B2

(12) United States Patent
Hmila et al.

(10) Patent No.: US 12,767,950 B2
(45) Date of Patent: Oct. 20, 2026

(54) DNA APTAMERS AND COMPOSITIONS TARGETING α-SYNUCLEIN AND METHODS OF MAKING AND USING SAME

(71) Applicant: Qatar Foundation for Education, Science and Community Development, Doha (QA)

(72) Inventors: Issam Hmila, Doha (QA); Omar El-Agnaf, Doha (QA)

(73) Assignee: HAMAD BIN KHALIFA UNIVERSITY, Doha (QA)

( * ) Notice: Subject to any disclaimer, the term of this patent is extended or adjusted under 35 U.S.C. 154(b) by 558 days.

(21) Appl. No.: 18/278,255

(22) PCT Filed: Feb. 19, 2022

(86) PCT No.: PCT/QA2022/050003
§ 371 (c)(1),
(2) Date: Aug. 22, 2023

(87) PCT Pub. No.: WO2022/177456
PCT Pub. Date: Aug. 25, 2022

(65) Prior Publication Data

US 2024/0124883 A1 Apr. 18, 2024

Related U.S. Application Data

(60) Provisional application No. 63/152,095, filed on Feb. 22, 2021.

(51) Int. Cl.
*C12N 15/115* (2010.01)
*C12N 15/10* (2006.01)

(52) U.S. Cl.
CPC ........ *C12N 15/115* (2013.01); *C12N 15/1048* (2013.01); *C12N 2310/16* (2013.01)

(58) Field of Classification Search
CPC .............. C12N 15/115; C12N 15/1048; C12N 2310/16; A61P 25/16; A61P 3/00
See application file for complete search history.

(56) References Cited

U.S. PATENT DOCUMENTS

2004/0123343 A1* 6/2004 La Rosa .............. C07K 14/415 800/278

OTHER PUBLICATIONS

Ren (Molecular Therapy Nucleic Acids 17 (2019): 726-740) (Year: 2019).*
Uchikado (Journal of Neuropathology & Experimental Neurology 65.7 (2006): 685-697) (Year: 2006).*
International Search Report for related International Application No. PCT/QA2022/050003; action dated Aug. 25, 2022; (8 pages).
Written Opinion for related International Application No. PCT/QA2022/050003; action dated Aug. 25, 2022; (5 pages).
Ren, X., Zhao, Y., Xue, F, Zheng, Y., Huang, H., Wang, W., Chang, Y., Yang, H. & Zhang, J. (2019). Exosomal DNA Aptamer Targeting α-Synuclein Aggregates Reduced Neuropathological Deficits in a Mouse Parkinson's Disease Model. Mol Ther Nucleic Acids, 17, 726-740. 10.1016/j.omtn.2019.07.008.
Callahan, J . . . The Selection of DNA Aptamers for the Prevention of Alpha-Synuclein Aggregation as a Therapeutic Tool In Parkinson's Disease . . . 10.22215/etd/2017-12144.
Zheng, Y., Qu, J., Xue, F, Zheng, Y., Yang, B., Chang, Y., Yang, H. & Zhang, J. (2018). Novel DNA Aptamers for Parkinson's Disease Treatment Inhibit α-Synuclein Aggregation and Facilitate its Degradation. Mol Ther Nucleic Acids, 11, 228-242. 10.1016/j.omtn.2018.02.011.

* cited by examiner

*Primary Examiner* — Neil P Hammell
*Assistant Examiner* — Kyle T Rega
(74) *Attorney, Agent, or Firm* — K&L Gates LLP

(57) ABSTRACT

The present disclosure, in part, relates to novel, aptamers targeting α-synuclein. The present disclosure includes methods for making and methods of using aptamers targeting α-synuclein.

18 Claims, 6 Drawing Sheets

Specification includes a Sequence Listing.

SEQUENCE LISTING

```
<160> NUMBER OF SEQ ID NOS: 8

<210> SEQ ID NO 1
<211> LENGTH: 39
<212> TYPE: DNA
<213> ORGANISM: Artificial Sequence
<220> FEATURE:
<223> OTHER INFORMATION: Aptamer Apt3

<400> SEQUENCE: 1

cgggctttgt tatcctgatg ctcctccttc ctaccactc                            39


<210> SEQ ID NO 2
<211> LENGTH: 40
<212> TYPE: DNA
<213> ORGANISM: Artificial Sequence
<220> FEATURE:
<223> OTHER INFORMATION: Aptamer Apt5

<400> SEQUENCE: 2

agggtctctt tcgttttggt gtatgtttct tcattatcgg                           40
```

-continued

```
<210> SEQ ID NO 3
<211> LENGTH: 40
<212> TYPE: DNA
<213> ORGANISM: Artificial Sequence
<220> FEATURE:
<223> OTHER INFORMATION: Aptamer Apt7

<400> SEQUENCE: 3

ctagtgtcgc cttttgcctc gttgtctccc atttatctcg                          40


<210> SEQ ID NO 4
<211> LENGTH: 40
<212> TYPE: DNA
<213> ORGANISM: Artificial Sequence
<220> FEATURE:
<223> OTHER INFORMATION: Aptamer Apt9

<400> SEQUENCE: 4

tagcgttccc cctcactcct tggttggtca tcatcgtccc                          40


<210> SEQ ID NO 5
<211> LENGTH: 40
<212> TYPE: DNA
<213> ORGANISM: Artificial Sequence
<220> FEATURE:
<223> OTHER INFORMATION: Aptamer Apt11

<400> SEQUENCE: 5

ctgacactcg gctttttatc ttccctgctt cggtcctgtc                          40


<210> SEQ ID NO 6
<211> LENGTH: 40
<212> TYPE: DNA
<213> ORGANISM: Artificial Sequence
<220> FEATURE:
<223> OTHER INFORMATION: Aptamer Apt15

<400> SEQUENCE: 6

ctttcctttc ctgtccgctt cgataaccct tcacacatcc                          40


<210> SEQ ID NO 7
<211> LENGTH: 40
<212> TYPE: DNA
<213> ORGANISM: Artificial Sequence
<220> FEATURE:
<223> OTHER INFORMATION: Aptamer Apt18

<400> SEQUENCE: 7

cgcctctgtc aagtccttat tcacgtctca gtccctccta                          40


<210> SEQ ID NO 8
<211> LENGTH: 40
<212> TYPE: DNA
<213> ORGANISM: Artificial Sequence
<220> FEATURE:
<223> OTHER INFORMATION: Aptamer Apt20

<400> SEQUENCE: 8

ccatcacaca ccattgttca ctccctgtct ctcgcacgct                          40
```

DNA APTAMERS AND COMPOSITIONS TARGETING α-SYNUCLEIN AND METHODS OF MAKING AND USING SAME

CROSS-REFERENCE TO RELATED APPLICATIONS

This application is a National Stage filing under 35 U.S.C. 371 of International Application No. PCT/QA2022/050003, filed on Feb. 19, 2022 which claims priority of U.S. Provisional Patent Application No. 63/152,095, filed Feb. 22, 2021, the entire content of which is incorporated herein by reference.

BACKGROUND

Parkinson's disease (PD) is a degenerative disorder that affects predominantly the dopaminergic neurons in the substantia nigra. The main protein implicated in PD is alpha synuclein (a-syn), which is found abundantly in the Lewy bodies (LBs) and Lewy neurites as aggregated forms that are the hallmark of pathological inclusions associated with PD. Accumulation of a-syn in LBs eventually leads to neuronal cell death and subsequently to behavioral and motor deficits. α-Syn is also linked to other neurodegenerative disorders like multiple system atrophy (MSA), dementia with Lewy bodies (DLB) and some variants of Alzheimer's which present LB pathology, all of which are collectively referred to as synucleinopathies. The 140-amino acid long a-syn protein comprises mainly three regions:

1. the N-terminal region (amino acids 1-60) having an apolipoprotein binding motif which is rich in lysine residues and able to bind to membrane components;
2. the NAC region (amino acids 61-95) enriched in hydrophobic residues and playing a central role in aggregation of protein; and
3. the C-terminal region (amino acids 96-140) containing many acidic residues and is, thus negatively charged and is implicated in protein aggregation.

LBs were also found to have different forms of a-syn with several post translational modifications. In addition to the full length a-syn, many truncated forms of a-syn have been found in pathological aggregates. Moreover, the C-terminal truncated a-syn is found to be more prone to aggregation in vitro and can facilitate the aggregation of the full-length protein in vitro and in vivo and induce neuronal toxicity. This suggests that these truncated a-syn forms might lead to the development of clinical and pathological features of PD.

The accumulation of a-syn in pathological inclusions and its propensity to drive aggregation by seeding further a-syn deposition and fibrillation make it the main target for the treatment of PD. To clear the a-syn aggregation linked pathology, many approaches have been pursued, such as inhibition of the a-syn fibrillation process by small molecules, lowering the protein level of a-syn by RNA interference or enhancing cellular degradation process. Another widely used approach is immunotherapy which relies on specific a-syn antibodies to tackle PD pathology, and some of these are in clinical trial phase. However, because of their size and nature, antibodies have limitations when applied in immunotherapeutic approaches for neurodegenerative diseases. For example, antibodies cannot easily access the intracellular compartments, cannot cross blood-brain barrier and also have higher immunogenicity. To circumvent these limitations, nucleic acid-based aptamers hold a great potential to be used as a promising approach for immunotherapy.

SUMMARY

The present disclosure, in part, relates to novel single-stranded DNA (ssDNA) aptamers targeting fibrillar forms of truncated a-syn. Aptamers are single stranded oligonucleotides isolated from random nucleic acids sequences (20-80 bp). Aptamers can bind to a wide range of targets ranging from simple inorganic molecules to large protein complexes and cells with high affinity and specificity. Compared to antibodies, aptamers offer many advantages including their non-immunogenic and non-toxic nature and their high thermal stability, and can maintain their structural integrity over repeated cycles of denaturation and renaturation. Moreover, their generation, synthesis and modification are cheaper than that of a conventional antibody.

Thus, there is a need for aptamers targeting fibrillar forms of truncated a-syn in PD.

The present disclosure also relates, in part, to novel methods of using ssDNA aptamers as methods of treatment.

DETAILED DESCRIPTION

Definitions

Figure 1:
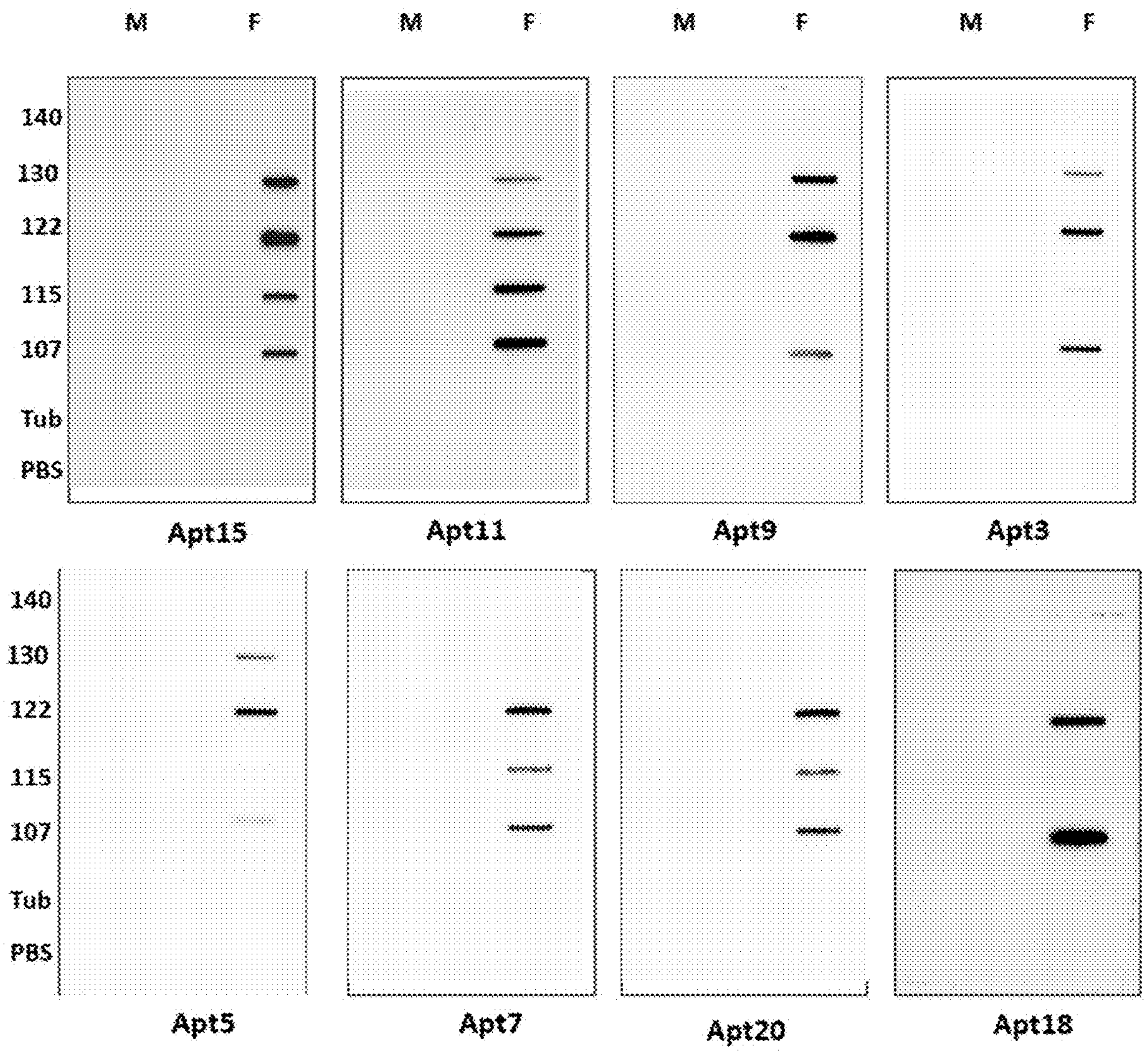
FIG. 1 shows a slot blot showing reactivity of aptamers to monomers and fibrils of full length (140) and truncated (130, 122, 115, 107) a-syn. Tubulin (Tub) was used as negative control.

Some definitions are provided hereafter. Nevertheless, definitions may be located in the "Embodiments" section below, and the above header "Definitions" does not mean that such disclosures in the "Embodiments" section are not definitions.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

A "subject" or "individual" is a mammal, preferably a human.

The term "unit dosage form," as used herein, refers to physically discrete units suitable as unitary dosages for subjects, each unit containing a predetermined quantity of the composition disclosed herein in amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

The term "sterile" is understood to mean free from any bacteria or other living microorganisms.

The term "pharmaceutically acceptable" as used herein refers to substances that do not cause substantial adverse allergic or immunological reactions when administered to a subject.

All percentages expressed herein are by weight of the total weight of the composition unless expressed otherwise. When reference herein is made to the pH, values correspond to pH measured at about 25° C. with standard equipment. "Ambient temperature" or "room temperature" is between about 15° C. and about 25° C., and ambient pressure is about 100 kPa.

The term "mM", as used herein, refers to a molar concentration unit of an aqueous solution, which is mmol/L. For example, 1.0 mM equals 1.0 mmol/L.

The terms "substantially no," "essentially free" or "substantially free" as used in reference to a particular component means that any of the component present constitutes no more than about 3.0% by weight, such as no more than about 2.0% by weight, no more than about 1.0% by weight, preferably no more than about 0.5% by weight or, more preferably, no more than about 0.1% by weight.

EMBODIMENTS

Various non-exhaustive, non-limiting aspects and embodiments of compositions according to the present disclosure may be useful alone or in combination with one or more other aspects and embodiments described herein. Without limiting the foregoing description, disclosed embodiments comprise methods of making an ssDNA aptamer. For example, in embodiments, the ssDNA aptamer can comprise an aptamer comprising a nucleotide sequence as set forth in Table 1, or combinations thereof. In embodiments, the ssDNA aptamer is specific for, for example, α-syn.

In further embodiments the ssDNA aptamer is specific for specific forms of a-syn, for example fibrillar forms of truncated α-syn.

In further embodiments, the ssDNA aptamer is not specific for monomers and fibrils of amyloid beta (Abeta 42), Islet amyloid polypeptide precursor (IAPP), amyloid Bri (ABri), β-syn, and/or γ-syn.

Further embodiments comprise methods of using an ssDNA aptamer, for example an ssDNA aptamer having a nucleotide sequence set forth in Table 1.

In embodiments, the ssDNA aptamer has an inhibitory effect on α-syn aggregation in vivo and/or in vitro.

In further embodiments, the ssDNA aptamer has an inhibitory effect on the phosphorylation of α-syn in vivo and/or in vitro.

Further embodiments comprise methods of treatment of a subject suffering from a synucleinopathy such as PD, comprising the step of administering to the subject a pharmaceutical composition comprising an effective amount of an a ssDNA aptamer, the ssDNA aptamer having a nucleotide sequence set forth in Table 1:

| | Sequence (5'→3') | Reads | RPM | Cluster number | Rank of sequence within cluster | Leven-shtein edit distance |
|---|---|---|---|---|---|---|
| Apt3 | CGGGCTTTGTTATCCTGATG CTCCTCCTTCCTACCACTC | 201568 | 54631.68 | 3 | 1 | 0 |
| Apt5 | AGGGTCTCTTTCGTTTTGGT GTATGTTTCTTCATTATCGG | 63037 | 17085.14 | 5 | 1 | 0 |
| Apt7 | CTAGTGTCGCCTTTTGCCTC GTTGTCTCCCATTTATCTCG | 41353 | 11208.05 | 7 | 1 | 0 |
| Apt9 | TAGCGTTCCCCCTCACTCCT TGGTTGGTCATCATCGTCCC | 22587 | 6121.83 | 9 | 1 | 0 |
| Apt11 | CTGACACTCGGCTTTTTATC TTCCCTGCTTCGGTCCTGTC | 67523 | 10775.96 | 11 | 1 | 0 |
| Apt15 | CTTTCCTTTCCTGTCCGCTT CGATAACCCTTCACACATCC | 8362 | 2266.38 | 15 | 1 | 0 |
| Apt18 | CGCCTCTGTCAAGTCCTTAT TCACGTCTCAGTCCCTCCTA | 7313 | 1982.07 | 18 | 1 | 0 |
| Apt20 | CCATCACACACCATTGTTCA CTCCCTGTCTCTCGCACGCT | 5721 | 1550.58 | 20 | 1 | 0 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXAMPLES

Example 1

Parkinson's disease (PD) is a progressive neurological disorder causing degeneration of affected neurons and is characterized by the accumulation of insoluble aggregates of α-synuclein (α-syn) in the Lewy bodies (LBs). In addition to full length a-syn aggregates, C-terminal truncated α-syn are abundant in the LBs. These truncated forms have been shown to act as seeds and facilitate the aggregation of the full-length a-syn in vitro and induce in vivo toxicity. Hence, identifying molecules that can inhibit the seeding activity of these truncated forms is of great importance. Here, we report the first in-vitro selection of aptamers targeting the aggregated forms of different C-terminal truncated α-syn using systematic evolution by exponential enrichment (SELEX) method followed by quantitative high-throughput DNA sequencing. We identified a panel of aptamers that bound with high specificity to different truncated forms of α-syn fibrils with no cross-reactivity towards others amyloid proteins including Abeta42, IAPP or ABri. Interestingly, two of the aptamers showed high affinity to most of the truncated forms of α-syn, inhibit α-syn seeded aggregation in vitro and reduced the phosphorylation of α-syn at Ser-129 (pS129-α-syn) in cells. The aptamers described here can be utilized as tools to various diagnostics or therapeutics strategies towards PD.

I—Introduction

Parkinson's disease (PD) is a degenerative disorder that affects predominantly the dopaminergic neurons in the substantia nigra. The main protein implicated in PD is alpha synuclein (α-syn), which is found abundantly in the Lewy bodies (LBs) and Lewy neurites as aggregated forms that are the hallmark pathological inclusions associated with PD. Accumulation of α-syn in LBs eventually leads to neuronal cell death and subsequently to behavioral and motor deficits. α-Syn is also linked to other neurodegenerative disorders such as multiple system atrophy (MSA), dementia with Lewy bodies (DLB) and some variants of Alzheimer's which present LB pathology, all of which are collectively referred to as synucleinopathies. The 140-amino acid long α-syn protein comprises mainly three regions: i) The N-terminal region (1-60 amino acids) having an apolipoprotein binding motif which is rich in lysine residues and able to bind to membrane components; ii) the NAC region (61-95 amino acids) enriched in hydrophobic residues and playing a central role in aggregation of protein; and iii) the C-terminal region (96-140 amino acids) containing many acidic residues and is, thus negatively charged and is implicated in protein aggregation.

LBs were also found to have different forms of α-syn with several post translational modifications. In addition to the full length α-syn, many truncated forms of a-syn have been found in pathological aggregates. Moreover, the C-terminal truncated a-syn is found to be more prone to aggregation in vitro and can facilitate the aggregation of the full-length protein in vitro and in vivo and induce neuronal toxicity. This suggests that these truncated α-syn forms might lead to the development of clinical and pathological features of PD.

The accumulation of α-syn in pathological inclusions and its propensity to drive aggregation by seeding further α-syn deposition and fibrillation make it the main target for the treatment of PD. To clear the α-syn aggregation linked pathology, many approaches have been tried, such as inhibition of the α-syn fibrillation process by small molecules, lowering the protein level of α-syn by RNA interference or enhancing cellular degradation process. Another widely used approach is immunotherapy which relies on specific α-syn antibodies to tackle PD pathology and some of these are in clinical trial phase. However, because of their size and nature, antibodies have some limitations when applied in immunotherapeutic approaches for neurodegenerative diseases. Antibodies cannot easily access the intracellular compartments, cannot cross blood-brain barrier and also have higher immunogenicity. To circumvent these limitations, nucleic acid-based aptamers hold a great potential to be used as a promising approach for immunotherapy.

Aptamers are single stranded oligonucleotides isolated from random nucleic acids sequences (20-80 bp) through an in vitro screening assay named Systematic Evolution of Ligand by EXponential Enrichment (SELEX). Aptamers can bind to a wide range of targets ranging from simple inorganic molecules to large protein complexes and cells with high affinity and specificity. Compared to antibodies, aptamers offer many advantages including their non-immunogenic and non-toxic nature, their high thermal stability and can maintain their structural integrity over repeated cycles of denaturation and renaturation. Moreover, their generation, synthesis and modification are cheaper than that of a conventional antibody. Many aptamers were generated for therapy and some of them are enrolled in clinical trials. One of the aptamers is already approved for the treatment of age related macular degeneration. For PD, aptamers were selected against dopamine to use it as a tool for biosensor for assessing dopamine neurotransmitter levels in serum. Aptamers have also been generated against α-syn protein. These aptamers have demonstrated their ability to bind selectively and specifically to α-syn oligomers to act as aptasensors for detection of oligomeric form of the protein. Some aptamers were also shown to effectively reduce α-syn aggregation in vitro and in cells and target the a-syn to intracellular degradation Recently, aptamers targeting α-syn aggregates were efficiently delivered into the mouse brain by the RVG-exosomes and were found to reduce neuropathological and behavioral deficits in vivo.

In this study, we identified aptamers against fibrillar forms of truncated α-syn as new target in PD. Aptamers described here were characterized for their specificity by various biochemical assays. The effect of aptamers on the seeding dependent aggregation and formation of insoluble phosphorylated α-syn in cell model, and their ability to block α-syn aggregation in-vitro were also studied.

Material and Methods

Expression and Purification of α-Syn

Full-length recombinant human α-syn (α-syn 140) was expressed in *Escherichia coli* BL21 (DE3) using the bacterial expression vector pRK172. Truncated a-syn (α-syn 130, α-syn 122, α-syn 115 and α-syn107) was expressed in *Escherichia coli* BL21 (DE3) using the bacterial expression vector pET3a. Following expression and sedimentation, the bacterial pellets from 1 L of TB (for α-syn 140) or LB (for truncated forms) media were homogenized and sonicated in 50 ml of high-salt buffer (750 mM NaCl, 10 mM Tris, pH 7.6, 1 mM EDTA) containing a cocktail of protease inhibitors, heated to 100° C. for 10 min, and centrifuged at 5300 rpm for 20 min. The supernatant was separated, dialyzed overnight against gel filtration buffer (50 mM NaCl, 10 mM Tris, pH 7.6, 1 mM EDTA) and the volume was reduced to 5 ml using Pierce protein concentrator (3K MWCO, ThermoFisher Scientific). All proteins were purified by size exclusion using a Superdex 200 gel filtration column (GE Healthcare). Except for α-syn 107, the clean fractions were pooled, exchanged with buffer (25 mM NaCl, 10 mM Tris pH 7.6, 1 mM EDTA, 1 mM PMSF) for ion exchange chromatography by dialysis overnight and were applied onto a HiTrap Q column (GE Healthcare) and eluted in 10 mM Tris pH 7.6 using a linear gradient of 25 mM to 1 M NaCl. Purified fractions were pooled and protein concentrations were determined using the Pierce BCA protein assay kit (ThermoFisher Scientific).

Preparation of α-Syn 122 Pure Seeds

α-Syn 122 monomers was incubated for 7 days at 37° C. with continuous shaking at 800 rpm in a thermomixer. The fibrils formed were pelleted by centrifugation at 14,000 rpm for 15 minutes at 4° C. The pellet was washed twice by resuspending in PBS, pH 7.4 followed by centrifugation at 14,000 rpm for 15 minutes at 4° C. The pellet is finally resuspended in PBS, pH 7.4 and sonicated (pulse 40, power output 40-50, 2 sec ON, 2 sec OFF, 5 min) to get pure seeds. The concentration of the pure seeds was then measured by BCA assay by solubilizing the pure seeds in 3M GnHCl.

Systematic Evolution of Ligands by Exponential Enrichment (SELEX)

Aptamers specific to C-terminal truncated form of α-syn ending at residue 122 (α-syn 122) were selected from a single-stranded DNA aptamer library using a slightly modified SELEX protocol reported by Hmila et al. The random DNA library (WAP40m) consisted of 80 nucleotides (nt) containing a 40 nt randomized central region flanked by two adaptor sequence regions each of 20 nt (Integrated DNA Technologies, Inc., Coralville, IA). The library sequence is 5'-AGTGCAAGCAGTATTCGGTC-(N40)-TAAAGCT-GATGCGTGATGCC-3'. SELEX was initiated with the immobilization of α-syn 122 in wells of a 96-well microtiter plate. Then, 100 μL of single-stranded aptamer DNA library (10 μM) was added to the protein coated at and incubated for 1 h.

The wells were then washed by adding 100 μL of 1×PBS and incubated for 5 min at room temperature (RT). Using a gradient of salt (NaCl) gradient elution, the wells were washed using six different concentrations of 0.5, 1.0, 1.2, 1.4, 1.5 M and 2M of NaCl. Then, 2 μl of the eluted DNA oligonucleotides from the 2M NaCl was amplified by symmetric PCR by an initial heat step for 5 min at 95° C. followed by 25 PCR cycles of 95° C. for 30 s, 55° C. for 30 s, 72° C. for 30 s and a final extension step at 72° C. for 7 min. The reaction mixture contained 5 μl of 10×PCR buffer, 2 μl of SELEX output pool, 0.5 μl (10 μM) of each forward WP20F1 (AGT-GCA-AGC-AGT-ATT-CGG-TC) and reverse primers WP20R1 (TAA-AGC-TGA-TGC-GTG-ATG-CC) (Integrated DNA Technologies, Inc., Coralville, IA), 1 μL of dNTP (10 mM) (Thermo Fisher Scientific), 0.5 μl Taq polymerase (Roche) and the volume was adjusted to 50 μl with deionized water.

An asymmetric PCR was performed then using 2 μL of symmetric PCR product as template and biotinylated forward primer and reverse primers of ratio 25:1 respectively. The thermocycler was initiated with a heating step for 5 min at 95° C. followed by a first 9 cycles of 95° C. for 30 s, 63° C. for 15 s, 72° C. for 15 s, and a subsequent 10 cycles of 95° C. for 30 s, 55° C. for 15 s, 72° C. for 15 s, and a final step of 72° C. for 3 min. The PCR product of the second PCR was used to recognize the protein immobilized on membrane nitrocellulose.

Purified truncated α-syn fibrils were immobilized on a nitrocellulose membrane and blocked with 5% skim milk in PBS-T. The product of asymmetric PCR was incubated on a nitrocellulose membrane that spotted with protein for 1 h. To detect the specific binding of the PCR product to α-syn fibrils coated, the membrane incubated with the PCR product was washed with PBS-T, and detection was performed using Streptavidin_HRP (sigma) at a 5000-fold dilution using PBS-T. The membrane was washed three times with PBS-T and developed using West Pico Western chemiluminescent HRP substrate (Thermofisher). DNA from the immobilized spots was extracted and PCR-amplified again by the same protocol. This screening was repeated five times. The PCR product from the last screening was then sequenced.

High-Throughput Sequencing Technology

The out-put of the SELEX amplified products via PCR using WP20F1 and WP20R1 primers were purified with the MinElute® PCR Purification Kit (Qiagen). The PCR amplicons were used as input for the library preparation. Briefly, the PCR amplicons were end-repaired and adenylated. Barcoded DNA adapters were ligated to both ends of the double-stranded cDNA and then amplified. The libraries quality was checked on an Agilent 2100 Bioanalyzer system using a High Sensitivity DNA kit and quantified on a Qubit system. The libraries were pooled and sequenced on the Illumina MiSeq platform by using MiSeq Reagent Kit v3 (150-cycle).

Bioinformatics Analysis

FASTAptamer Tool kit was used following the steps described by authors (Alam, Chang, and Burke 2015). First, the fastaptamer_count package was used to rank and sort the sequences by their abundance and which is normalized for reads per million (RPM). Second, the fastaptamer_cluster was used to align and classify the reads by sequence similarity. Finally, sorted sequences were evaluated for their affinity and specificity.

Slot Blot Assay

The slot blot system was assembled with a pre-wet 0.2 μm nitrocellulose membrane following the manufacturer's protocol. 1 μg of the truncated or full-length a-syn in 50 μl PBS was applied to each slot. Following this, the wells were washed with 1000 μl PBS and the membrane was then air dried for 45 minutes. The dried membrane was blocked with 5% skimmed milk in PBST (PBS containing 0.05% Tween 20) for 1 h at RT. After blocking, the membranes were incubated overnight in the respective biotin tagged aptamer at 4° C. Following washes with PBST, membranes are incubated in secondary antibody (Streptavidin-HRP) for 1 h at RT. After final washes, the membranes are detected using west Pico chemiluminescent substrate and imaged using Biorad Imaging System.

Detection of Insoluble pS129 α-Syn in HEK293T Cell Model of PD

Human embryonic kidney (HEK293) cells were grown in Dulbecco's MEM-high glucose (Gibco BRL, Rockville, MD) supplemented by 15% fetal bovine serum (Gibco BRL, Rockville, MD) and 1% penicillin-streptomycin (Gibco BRL, Rockville, MD) with incubation at 37° C. in a 5% CO2/95% air humidified incubator. After plating the cells overnight, cells were transfected with 2 μg of WT α-syn plasmid DNA using lipofectamine 3000 reagent (Invitrogen, Waltham, MA). One group of α-syn expressing HEK cells was similarly transfected again with 4 μg of α-syn 122 seeds the following day and then incubated with aptamers (11 and 15) in OptiMEM (Gibco BRL, Rockville, MD) for 48 hours at seeds: aptamer molar ratio of 1:1 and 1:5.

The other group of cells were transfected with both aptamers and seeds at molar ratio of 1:1 and 1:5 by lipofectamine 3000 after one hour of incubation at 37° C. and shaking at 800 RPM. HEK cells were lysed, 48 hours post transfection, initially with 1% Trition X-100 in 50 mM Tris, 150 mM NaCl (pH 7.6) containing protease and phosphatase inhibitors to obtain soluble fractions. The pellet was further lysed with 1% SDS in 50 mM Tris, 150 mM NaCl (pH 7.6) with complete inhibitors to attain insoluble fractions.

Protein concentration was determined by BCA protein assay (Pierce) prior to analysis on 12% SDS-PAGE and immunoprobing with certain antibodies. These include monoclonal antibodies against rabbit phospho S129 alpha-synuclein (AB51253) (Abcam, Cambridge, MA) and mouse alpha235 synuclein Syn1 (610786) (BD Biosciences, San Jose, CA), in addition to antibodies against p-Actin (C4) (Sc-47778) (Santa Cruz Biotechnology, Dallas, TX) to normalize for the amount of proteins. Blots were later incubated with horseradish peroxidase conjugated with anti-rabbit and anti-mouse IgG (Jackson Immuno Research, West Grove, PA), and proteins were detected.

Seeded Polymerization Assay and Th-S Assay

α-Syn 122 seeds (1 μM) were added to 25 μM monomeric α-syn and incubated in the presence or absence of aptamers (seeds: aptamer molar ratio of 1:1, 1:5, and 1:20) at 37° C. for 48 hours with continuous shaking. The fibril formation was measured by Th-S binding assay. Th-S binding assay was used to study α-syn fibril formation. Being a fluorescent dye, Th-S interacts with fibrils containing p-sheet structures. Sample (10 μl) was diluted in 40 μl of Th-S (20 μM) in PBS and the mixture was dispensed in a 384-well, untreated black plate (Nunc, Denmark). The fluorescence was measured in a microplate reader (Victor X3 2030, Perkin Elmer) with the excitation and emission wavelengths at 450 and 510 nm, respectively.

Transmission Electron Microscopy

The samples (Sul) were deposited on Formvar-coated 200-mesh copper grids (Agar Scientific, UK), fixed briefly with 0.5% glutaraldehyde, washed with dd water, negatively stained with 2% uranyl acetate (Sigma) and imaged with a TalosF200C TEM electron microscope (FEI company) at 200 keV.

Western Blot

The samples were mixed with non-denaturing sample buffer (without any boiling and SDS) and separated on 12% SDS-PAGE gel. Proteins were transferred to nitrocellulose membrane and incubated with (FL140, Santa Cruz, anti-α-syn 1:1000 dilution) followed by incubation with HRP-conjugated IgG goat anti-rabbit antibody (Thermo Scientific) at a dilution of 1:10,000. Blots were imaged in Bio-Rad ChemiDoc MP imaging system using SuperSignal West-Pico-Chem iluminescent Substrate.

Results

Identifying Novel Aptamers Against Truncated α-Syn

To discover a novel aptamer, we used truncated α-syn 122 protein in SELEX based screening assay. After five cycles of SELEX, the output of the screening was analyzed by the FASTAptamers software. Using the command fastaptamer-_cluster, the closely related sequences were grouped in to clusters sorted by its rank, reads, RPM, cluster number, rank within that cluster and Levenshtein edit distance that reflects the number of insertions, substitutions, or deletions between sequences (Table 1). The first 20 clusters were chosen for further characterization to determine their activity against a-syn protein binding and detection.

Reactivity of Aptamers to Full Length and Truncated α-Syn Monomers and Fibrils

We tested the reactivity of selected aptamers from the library towards monomeric and fibrillar forms of full length (1-140 amino acids) and different truncated forms (1-130, 1-122, 1-115 and 1-107 amino acids) of α-syn in slot blot assay. From the 20 aptamers tested, 8 aptamers (Apt3, Apt5, Apt7, Apt9, Apt11, Apt15, Apt18 and Apt20) showed high and specific reactivity to α-syn fibrils. Interestingly, none of them showed reactivity to the full length α-syn fibrils but showed differential reactivity to the truncated fibrils of α-syn (FIG. 1). The full length α-syn has a C-terminal domain with a high negative charge which could probably be interfering with the binding of negatively charged DNA aptamers. This could explain the non-reactivity to the full-length protein and stronger reactivity to the truncated forms. Apt11 and Apt15 showed reactivity to all the truncated forms of α-syn, whereas Apt9, Apt3 and Apt5 showed reactivity only to α-syn 1-130, 1-122 and 1-107 proteins. Apt7, Apt20 showed reactivity to truncated forms 122, 115 and 107. Apt18 showed reactivity only to α-syn 122 and 107 proteins. None of the aptamers showed any reactivity to tubulin protein which we included as a negative control in the slot-blots (FIG. 1).

Testing the Specificity of Aptamers

Figure 2:
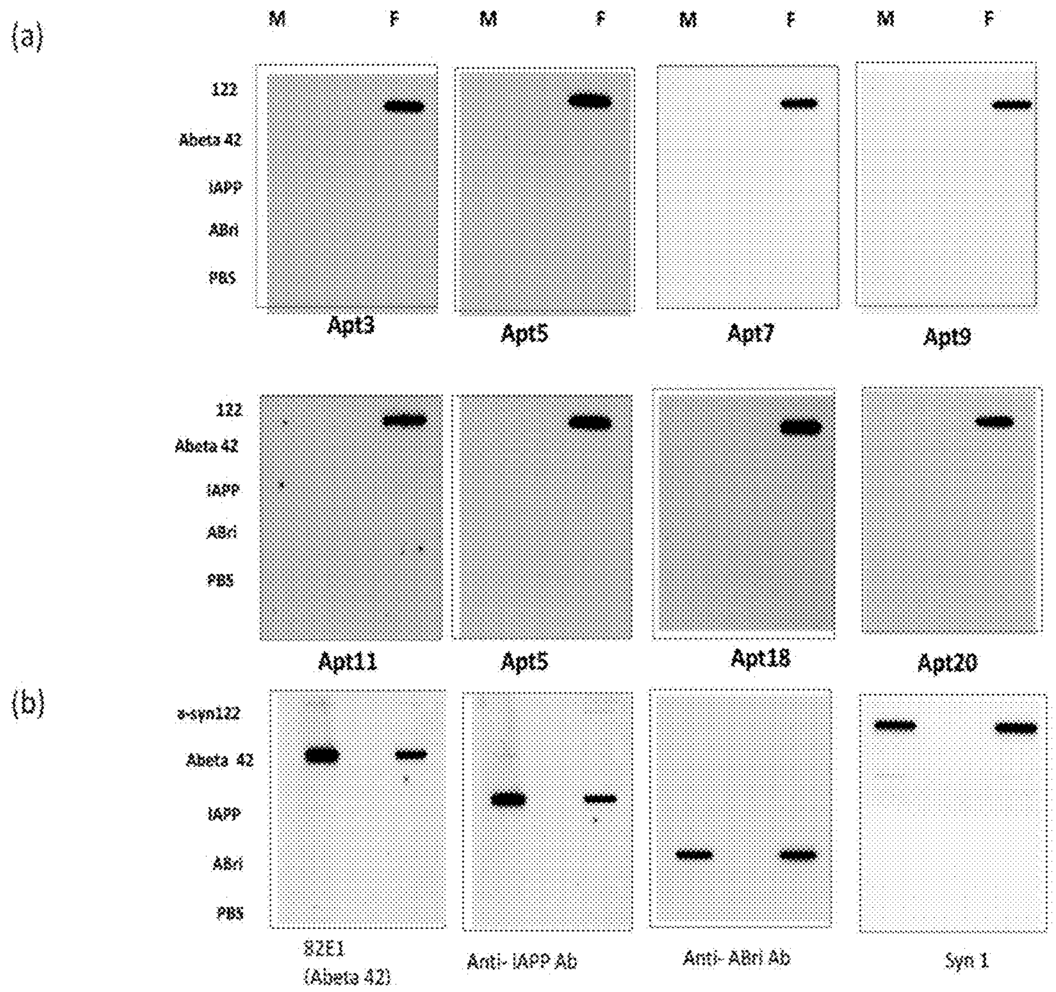
FIG. 2 shows slot blots showing reactivity of aptamers (FIG. 2A) or control antibodies (FIG. 2B) to a-syn 122 and other amyloid proteins Abeta42, IAPP and ABri.

In order to evaluate the specificity of aptamers for α-syn, we tested the reactivity of aptamers to monomers and fibrils of other amyloid proteins like amyloid beta (Abeta 42), Islet amyloid polypeptide precursor (IAPP) and amyloid Bri (ABri) (FIG. 2). None of the aptamers showed any reactivity to the fibrils of any of these amyloid proteins other than α-syn. This shows that our aptamers are specifically binding to the fibrillar conformation of α-syn rather than the generic beta-sheet structure found in amyloid proteins (FIG. 2). This contrasts with some previous reports from Tsukakoshi et al, where they observed that DNA aptamers raised against α-syn showed some level of reactivity to Abeta 40 oligomers.

Figure 3:
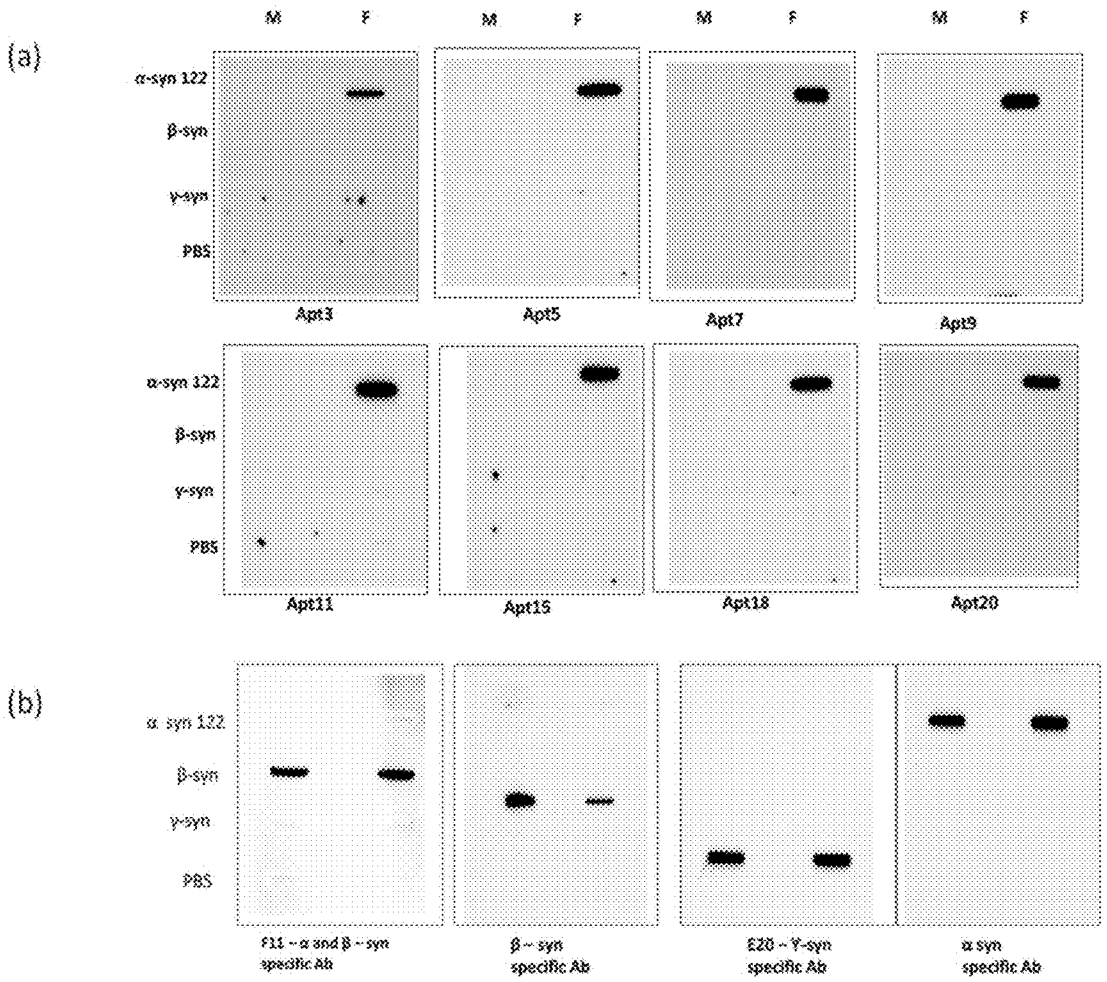
FIG. 3 shows slot blots showing reactivity of aptamers (FIG. 3A) or controls antibodies (FIG. 3B) to different synucleins (α-, β- and γ-syn).

We also assessed if these aptamers are specific to α-syn in comparison to other members of the synuclein family (P-syn and y-syn). We found that the reactivity of aptamers was specific to α-syn fibrils and they do not detect monomers or fibrils or β- and γ-syn (FIG. 3). Here, it is to be noted that the non-reactivity we observed could also be due to the negatively charged C-terminal domain present in the full length β-syn and y-syn that can potentially affect the binding of aptamers.

Effect of Apt11 and Apt15 Aptamers on α-Syn Aggregation

To investigate the effect of the aptamers on α-syn aggregation, α-syn 140 monomer was incubated with α-syn 122 seeds preincubated with different concentrations of aptamers. Th-S results showed that Apt11 and Apt15 were able to inhibit of α-syn fibril formation upon all three molar ratios during all time points (FIG. 4A, B) with Apt11 having a greater effect. This indicated that these aptamers have an inhibitory effect on a-syn aggregation.

Figure 5:
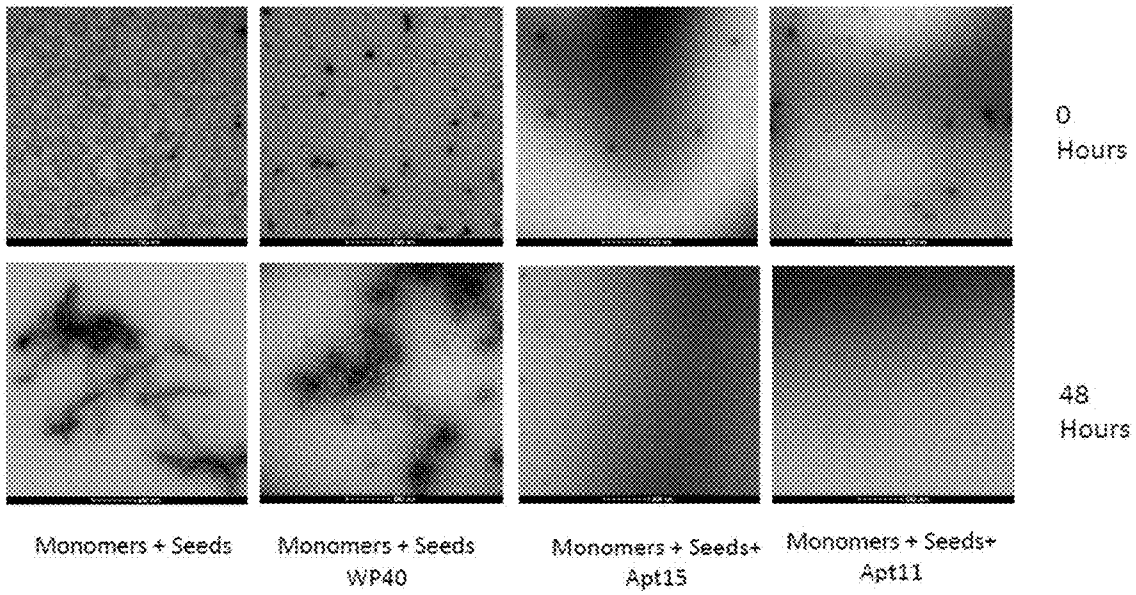
FIG. 5 shows electron microscopy images of negatively stained samples collected at time 0 and 48 hours from the inhibition aggregation assays show that mature amyloid fibrils (300-700 nm long) are formed in seeds and monomer incubated samples 48 hours' time point which is inhibited by Apt11 and Apt15. No inhibition was obtained by the library WP40 as negative control. Scale bar=500 nm.

These results were further confirmed by electron microscopy (FIG. 5) where incubation of α-syn monomers with α-syn 122 seeds preincubated with aptamers Apt11 and Apt15 showed absence of fibril formation whereas the control aptamer WP40 had no effect (FIG. 5). Similar results were obtained via western blotting using samples from in vitro seeding of α-syn aggregation assay (FIG. 6) which showed that incubation of Apt 11 and 15 inhibit formation of high molecular weight aggregate bands formed upon co-incubation of seeds and monomer at 48 hours time-point, whereas control aptamer, WP40 had no effect. Th-S assay, electron microscopy and western blotting, all three assays conclusively proved the inhibitory effect of Apt 11 and 15 on seeded aggregation of α-syn.

Figure 4:
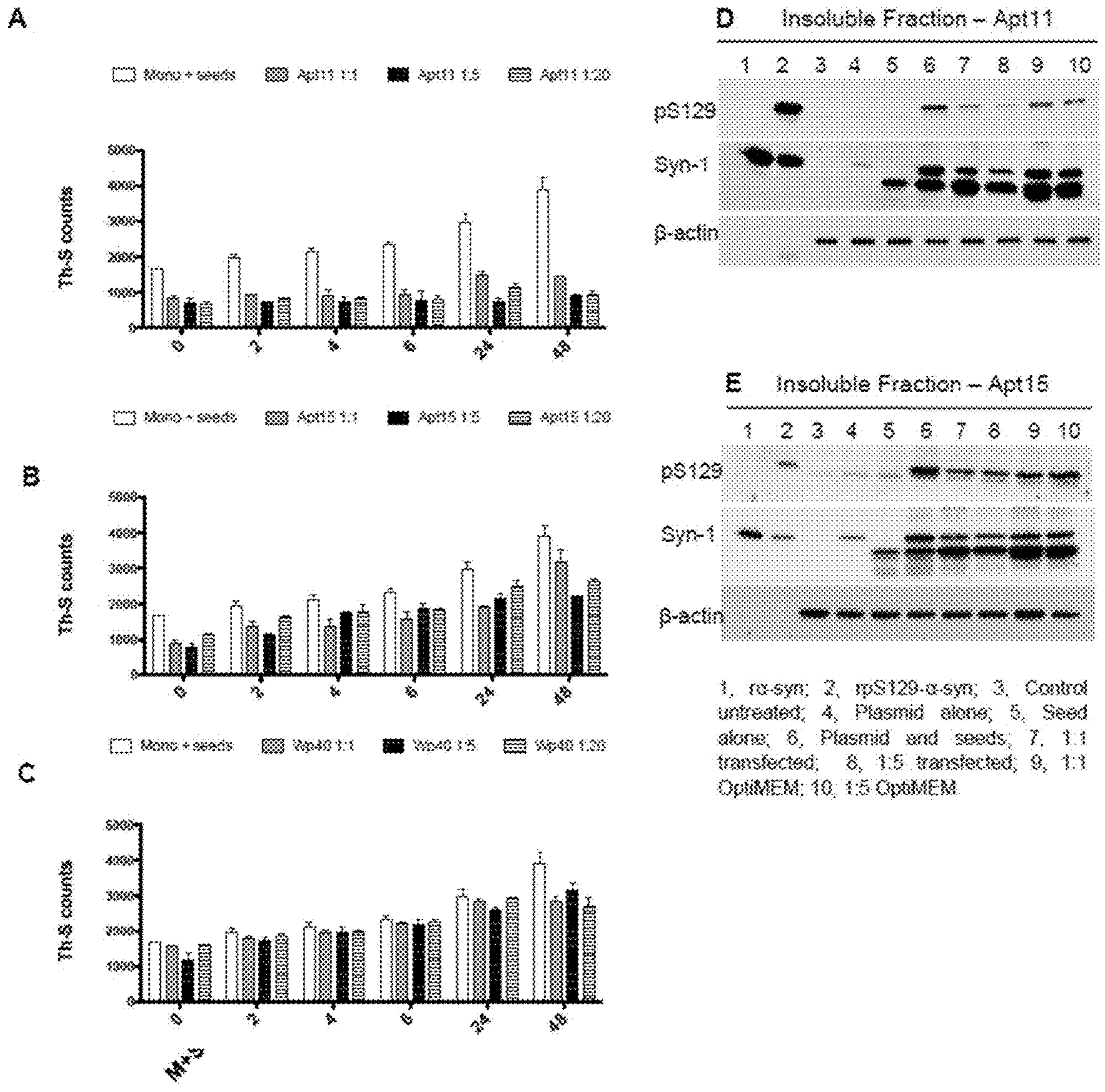
FIG. 4 shows the effect of Apt11 aptamers on seed induced a-syn aggregation. α-syn monomers incubated with a-syn S122 seeds alone or with S122 seeds and aptamers at three molar ratios, seeds: aptamers, (1:1, 1:5 and 1:20) up to 48 hours at 37° C. The fibril content was measured by Th-S binding assay. Effect of Apt11 (D) and Apt15 (E) on insoluble pS129-a-syn aggregation. Immunoblotting proteins from un-transfected (control) and transfected HEK cells from insoluble (10 μg) fractions. Fractions were assessed using antibodies specific to pS129-a-syn and total a-syn (Syn1). One of the transfected HEK cell groups was simultaneously transfected with a-syn-S122 seeds and aptamers (11 and 15) at 1:1 and 1:5 molar ratios after an incubation at 37° C. for one hour, the other group was transfected with S122 seeds to be followed by Apt11 and Apt15 treatment at 1:1 and 1:5 molar ratios in OptiMEM for 48 hours. Recombinant pS129 a-syn (rpS129-α-syn) and recombinant α-syn (r-α-syn) proteins (50 ng) were used as positive controls. Re-immunoblotting with β-actin antibody was performed to normalize the amount of loaded proteins.

Effect of Apt11 and Apt15 Aptamers on the Seeding Dependent Aggregation and Phosphorylation of α-Syn An in-vitro HEK cell model expressing α-syn was used to study the effect of aptamers on the seeding dependent aggregation and formation of insoluble phosphorylated α-syn at Ser 129 (pS129-α-syn). Apt11 significantly decreased the formation of insoluble pS129-α-syn in the four treated groups (FIG. 4D). Moreover, Apt15 also showed a decrease in the insoluble pS129-α-syn especially in the transfected group of both aptamers and seeds after one hour of incubation (FIG. 4E). This suggests that Apt11 and Apt15 have an inhibitory effect on the seeding dependent aggregation and phosphorylation of α-syn.

Real-Time Quaking-Induced Conversion (RT QuIC) Assay

The RT-QuIC assay was performed using purified recombinant truncated α-syn and modified from the previously described method. The reaction buffer was composed of 0.1 M PIPES (pH 6.9), 0.2 M NaCL, 0.1 mg/mL α-syn and 10 uM ThT. Reactions were performed in triplicate in black 96-well plates with a clear bottom (Nunc, Thermo Fischer) with 85 μL of the reaction mix loaded into each well together with 15 ul of 0.1 mg/ml brain homogenates and 10 uM of aptamers. The plate was then sealed with a sealing film (Thermo Fisher Scientific) and incubated in a BMG Labtech FLUOstar OMEGA plate reader at 37° C. for 90 hours with intermittent cycles of 1 min shaking (500 rpm, double orbital) and 5 min rest throughout the indicated incubation time. ThT fluorescence measurements, expressed as arbitrary relative fluorescence units (RFU), were taken with bottom reads every 15-min using 450±10 nm (excitation) and 480±10 nm (emission) wave-lengths. ThT fluorescence measurements, expressed as arbitrary relative fluorescence units (RFU), were taken with bottom reads every 30-min using 450±10 nm (excitation) and 480±10 nm (emission) wavelengths.

Effect of the Aptamers in the RT-QuIC Assay

Figure 6:
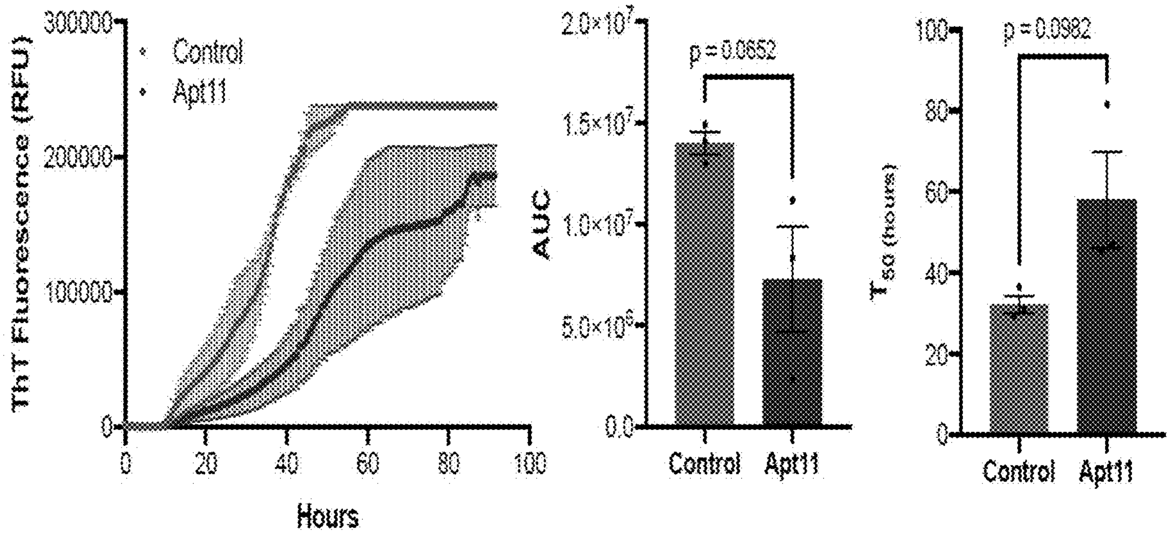
FIG. 6 shows RT-QuIC assays with and without Apt11 using brain homogenates from PD cases. Brain samples were prepared from 3 cases of PD, then assayed by RT-QuIC using with rec αSyn122 as described in the methods sections. Data shown are the averages (±SEM) of ThT area under the RT-QuIC curves (AUC) and the time to reach the 50% of the maximum fluorescence value (T50). Unpaired t-test with Welch's correction (GraphPad Prism) was used for statistical comparisons.

For extensive characterization using RT-QuIC assay, only Apt11 were tested as the best aptamer selected based on the inhibition of seeded aggregation and phosphorylation assays. The RT-QuIC assay is an in vitro α-syn amplification techniques using samples from patient containing pathogenic α-syn as seeds and the recombinant α-syn monomers. The fibrillary conversion products can be monitored in real time using the amyloid fibril-sensitive fluorescent dye, thioflavin T (ThT). An inhibitory effect of Apt11 was detected when the reaction is seeded with three different brain homogenates extracted from patients affected by PD and recombinant α-syn122 as a substrate. The average curves for α-syn aggregation from the RT-QuIC assays are shown in FIG. 6. The seeding response was decreased when Apt11 was applied in a concentration of 10 uM. Based on the time to reach half of the maximum fluorescence value (T50) and the Area Under the Curve (AUC), Apt11 showed an inhibitory effect on α-syn aggregation which was borderline significant (t-test, AUC $p=0.065$; T50 $p=0.098$).

Discussion

Recently, aptamers as ligand element have obtained increasing interest in the development of therapeutic and analytic methods. They can recognize a wide range of molecules with high affinity and specificity. Aptamers are simple molecules, can be rapidly synthesized, stable and cheaper than developing conventional antibodies. They are smaller than antibodies and can be more suitable for more efficiency to cross blood-brain barrier (BBB) and reach the central nervous system. The selection of aptamers is done from random sequences of nucleic acid library through SELEX in vitro. In this study, we used a special method for the selection based on the elution of high binding aptamer with high salt concentration of NaCl followed by amplification by PCR and blotting assay. This protocol have been shown to enrich high affinity aptamers with minimum rounds of selection.

Numerous studies have shown that truncation of α-syn at the N- or C-terminal region might have an important role in α-syn aggregation. α-Syn truncations are the most common post translational modifications representing upto 15% of total α-syn found in LBs. They have been found to be more prone to aggregation in vitro and in vivo than wild type. These forms induce the process of α-syn aggregation by an efficient seeding process of the full-length α-syn. For the first time, our study targets these truncated forms by developing specific aptamers with high specificity. They bind only to fibril forms and not the monomeric form of α-syn and did not recognize other amyloid proteins. This demonstrated that our aptamers are amino acids specific to truncated forms of α-syn. This is different to other works wherein aptamers recognized common structure of amyloid fibrils structure. Also, our aptamers do not show any binding to the full length a-syn. This is because of the negatively charged and exposed C-terminal region of the protein that can affect the binding of our aptamers. The selected aptamers showed varying affinities to the different truncated forms of α-syn. The possible reason could be the various conformations of truncated fibrils and different accessibility of the epitope recognized by aptamers. It has been previously reported that C-terminal truncated α-syn indeed formed fibrils with unique morphologies and they modulate the prion-like aggregation and seeding activity of full length α-syn. Interestingly, these aptamers were found to inhibit the aggregation of full-length α-syn protein when seeded with truncated α-syn 122 seeds.

Phosphorylation is another important post-translational modifications observed in α-syn. The hyper-phosphorylated forms of α-syn protein at S129 (pS129 α-syn) are the major components of Lewy bodies (LBs) and Lewy neurites found in the brains with PD and dementia with Lewy bodies. They represent almost 90% of aggregated α-syn in LBs compared to only 4% α-syn in normal cellular conditions. Previous works demonstrated that α-syn expression in presence of seeds lead to the formation of insoluble aggregates as detected by pSer129 staining. The incubation of our aptamers Apt11 and Apt15 with the seeds significantly reduced the levels of pSer129 α-syn in the insoluble fractions. Our findings suggest that these aptamers can be added to the panel of previous molecules that have viable therapeutic option for the treatment of synucleinopathies. Aptamers can be attractive target to be used in in vivo imaging applications as therapeutic or diagnostic tool towards synucleinopathies.

In conclusion, we selected high specific aptamers to truncated α-syn from random DNA library by an original protocol of SELEX. Aptamers selected showed high specificity to α-syn and did not cross react with other amyloid proteins. Two of the aptamers selected showed a high ability to inhibit the aggregation of full length α-syn promoted by the α-syn 122 seeds. It was also able to inhibit the induced phosphorylation of α-syn in insoluble fraction in cell model. This work demonstrates again the potency of aptamers as tool to build diagnostic and therapeutic reagent for PD.

Example 2

A patient is diagnosed with Parkinson's Disease. To treat the condition, the patient is administered an effective amount of an ssDNA aptamer.

Example 3

A patient is diagnosed with Alzheimer's Disease. To treat the condition, the patient is administered an effective amount of an ssDNA aptamer.

Example 4

A patient is diagnosed with dementia with Lewy bodys. To treat the condition, the patient is administered an effective amount of an ssDNA aptamer.

Example 5

A patient is diagnosed with multiple system atrophy (MSA). To treat the condition, the patient is administered an effective amount of an ssDNA aptamer.

The invention claimed is:

1. A method of treating a subject suffering from Parkinson's disease, comprising administering to the subject a pharmaceutical composition comprising an effective amount of an ssDNA aptamer, wherein said ssDNA aptamer comprises at least one of Apt3, Apt5, Apt7, Apt9, Apt11, Apt15, Apt18, or Apt20.

2. The method of claim 1, wherein said ssDNA aptamer comprises Apt3.

3. The method of claim 1, wherein said ssDNA aptamer comprises Apt5.

4. The method of claim 1, wherein said ssDNA aptamer comprises Apt7.

5. The method of claim 1, wherein said ssDNA aptamer comprises Apt9.

6. The method of claim 1, wherein said ssDNA aptamer comprises Apt11.

7. The method of claim 1, wherein said ssDNA aptamer comprises Apt15.

8. The method of claim 1, wherein said ssDNA aptamer comprises Apt18.

9. The method of claim 1, wherein said ssDNA aptamer comprises Apt20.

10. A composition comprising an ssDNA aptamer and a Pharmaceutically acceptable carrier, wherein said ssDNA aptamer comprises at least one of Apt3, Apt5, Apt7, Apt9, Apt11, Apt15, Apt18, or Apt20.

11. The composition of claim 10, wherein said ssDNA aptamer comprises Apt3.

12. The composition of claim 10, wherein said ssDNA aptamer comprises Apt5.

13. The composition of claim 10, wherein said ssDNA aptamer comprises Apt7.

14. The composition of claim 10, wherein said ssDNA aptamer comprises Apt9.

15. The composition of claim 10, wherein said ssDNA aptamer comprises Apt11.

16. The composition of claim 10, wherein said ssDNA aptamer comprises Apt15.

17. The composition of claim 10, wherein said ssDNA aptamer comprises Apt18.

18. The composition of claim 10, wherein said ssDNA aptamer comprises Apt20.

* * * * *